US00PP29361P2

(12) United States Plant Patent
Hansen

(10) Patent No.: US PP29,361 P2
(45) Date of Patent: Jun. 5, 2018

(54) ***HEUCHERA* PLANT NAMED 'PRETTY PISTACHIO'**

(50) Latin Name: ***Heuchera* hybrid**
Varietal Denomination: Pretty Pistachio

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,031

(22) Filed: Nov. 21, 2016

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
CPC ... A01H 5/02; A01H 5/12; A01H 5/00; A01H 5/025
See application file for complete search history.

(56) References Cited

PUBLICATIONS

Michell's Walters Gardens, Inc. 2015-2016 Availability List retrieved on Nov. 20, 2017, retrieved from the Internet at http://www.michells.com/availabilities/Waltersavailability.pdf, pp. 1, 15, 28.*

* cited by examiner

*Primary Examiner* — June Hwu

(57) ABSTRACT

The new and distinct hybrid of *Heuchera* plant named 'Pretty Pistachio' with foliage of yellowish lime green in summer. The new plant has medium a pink flower effect from showy persistent calyces and six to nine week flowering period. The new plant is vigorous, and produces large clumps and is useful in the landscape, in containers or as cut flower.

1 Drawing Sheet

Botanical denomination: *Heuchera* hybrid.
Variety denomination: 'Pretty Pistachio'.

BACKGROUND OF THE INVENTION

The present invention relates to a new and distinct cultivar of Coral Bells in the Saxifragaceae family and given the cultivar name of 'Pretty Pistachio'. *Heuchera* 'Pretty Pistachio' was hybridized by the inventor on Jan. 23, 2012 at a wholesale perennial nursery in Zeeland, Mich., USA and initially assigned the breeder code 12-139-2. The seed or female parent was *Heuchera* 'Hercules' (not patented) and the pollen or male parent was a proprietary unreleased hybrid known only by the breeder code K9-67-05. The male parent is a cross consisting of 'Tiramisu' U.S. Plant Pat. No. 20,429, 'Mocha' U.S. Plant Pat. No. 18,386 and 'Pistache' U.S. Plant Pat. No. 19,585.

*Heuchera* 'Pretty Pistachio' was first selected in the fall of 2012 and passed final evaluation in the fall of 2014 from among thousands of other seedlings from the same cross and hundreds of other crosses. *Heuchera* 'Pretty Pistachio' has been asexually propagated by division at the same nursery in Zeeland, Mich. in 2014 and by careful shoot tip tissue culture propagation, and the resultant plants have remained stable and continued to exhibit the same characteristics as the original plant for multiple generations.

No plants of *Heuchera* 'Pretty Pistachio' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

In comparison to the female parent, *Heuchera* 'Pretty Pistachio' has chartreuse to lime green foliage compared to the marbled variegation of green and cream of 'Hercules'. Compared to the named cultivars in the male side of the lineage the new plant does not develop the brick red coloration of the leaves of 'Tiramisu' and has medium pink flower rather than cream of 'Tiramisu'. In comparison, 'Mocha' has bronze purple foliage with royal purple undersides and the flowers are cream-colored. The lime-green to chartreuse foliage of 'Pistache' is similar but not as rounded in the lobe and the flowers of 'Pistache' are cream colored. Compared with the male parent, the new plant has larger, pinkish flowers and the male parent has smaller, greenish to cream-colored flowers, and the foliage of the male parent is more rugose with rounded lobe apices and does not develop as light chartreuse to yellow in color. Other similar coral bells include: 'Electric Lime' U.S. Plant Pat. No. 21,872 which has foliage with similar lime green, but the lobes of 'Electric Lime' are more acute, and the flowers are white rather than the medium pink of 'Pretty Pistachio'

*Heuchera* 'Pretty Pistachio' differs from its parents as well as all other coral bells known to the applicant in the following combined traits:

1. The large cordate leaf blades are yellowish lime green in summer with both surfaces matte.

2. Produces medium pink flowers with pink calyxes beginning early summer and lasting for six to nine weeks.
3. Panicles are dense with flowers and rise just above foliage.
4. Produces large clumps and many large individual leaves.
5. Plant is vigorous.

BRIEF DESCRIPTION OF THE DRAWINGS

The photographs of the new plant demonstrate the overall appearance of the plant including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
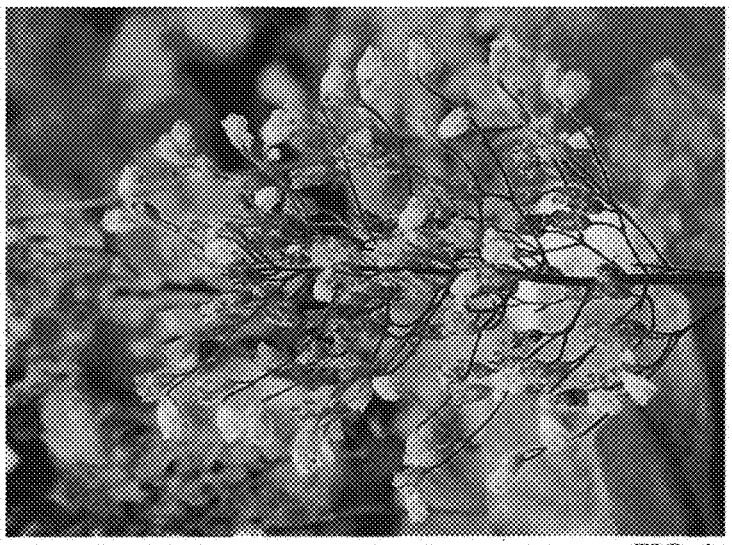
FIG. 1 shows a close-up of the flowers and buds.
Figure 2:
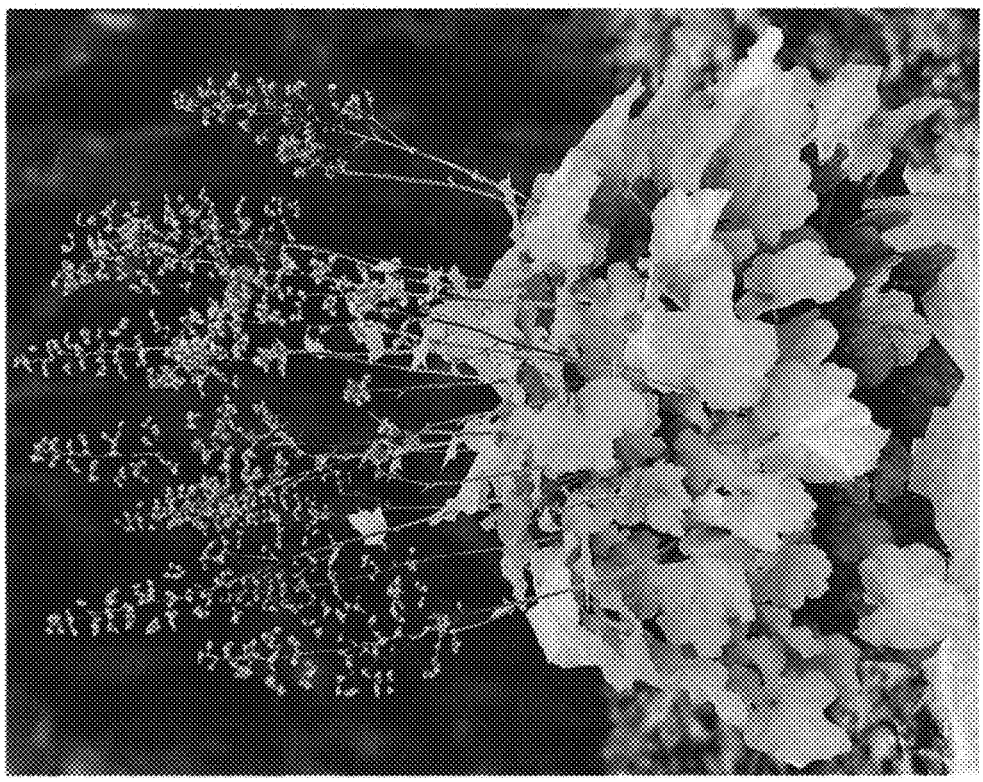
FIG. 2 shows a two-year-old plant in full flower.

The following description is based on a one-year-old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female or seed parent was *Heuchera* 'Hercules' (not patented) and the pollen or male parent was a proprietary unreleased hybrid known only by the breeder code K9-67-05 (not patented);

Plant habit: Hardy herbaceous perennial with basal rosette of foliage; mounded foliage about 20 cm tall and 38 cm in diameter with scapes to about 45 cm long; stems to about 4.0 cm long and 1.2 cm diameter at base with about 12 to 18 leaves per stem and six main sterns per plant;

Roots: Fibrous, finely branched;

Growth rate: Rapid, rooting from cutting in two weeks and finishing in three-liter container in about 3 months;

Foliage: Cordate, minutely puberulent adaxial and abaxial; palmately shallowly lobed with five main lobes dissected less than one-quarter the way to petiole; apex and lobes rounded, base cordate to auriculate with basal lobes infrequently overlapping about 0.5 cm; margins crenate to mucronate, hirsutulous, lustrous adaxial and abaxial; held nearly horizontal; marginal undulation weak;

Leaf blade size: To about 10.5 cm wide and 9.5 cm long, average about 9.5 cm wide and 9.0 cm long;

Leaf color: Spring and young emerging leaves adaxial nearest RHS N144A and with no silver or dark green marbling surrounding the veins, spring young emerging leaves abaxial nearest RHS 151A; mature mid-season leaves adaxial variable with some leaves nearest RHS 145A and others nearest RHS 153D with no marbling of silver or darker green surrounding the veins, abaxial mature mid-season leaves variable with some leaves lighter than RHS 146D and others nearest RHS 153C; mid-winter adaxial color variable with distal portion a mixture of nearest RHS 174B, RHS 176B and RHS 165C; toward petiole nearest RHS 160A becoming increasingly darker yellow-green to nearest RHS 146B adjacent to petiole; mid-winter abaxial color blotchy and variable with nearest RHS 182B distally and mixed with blotches and becoming solid RHS N148C toward petiole;

Leaf quantity: Dense, about 150 per plant;

Veins: Palmate, hirsutulous abaxial and puberulent adaxial; costate abaxial and nearly flat adaxial;

Vein color: On emerging or early spring foliage adaxial blend nearest RHS N144A with emerging or early spring abaxial nearest RHS 145C; mid-season and flowering time adaxial nearest RHS N144A, mid-season and flowering time abaxial between RHS 145C and RHS 145D;

Petiole: Terete, with base amplexicaul; with pubescent hairs to about 2.0 mm long; average about 10.0 cm long and about 2.5 mm diameter about stipule and 7.0 mm across at base including stipule;

Petiole color: Emerging leaf nearest RHS N170D with a darker adaxial stripe of nearest RHS 186B; mature leaf nearest RHS 145A with very light blush of nearest RHS 183D near base;

Stipule: At base of petiole, about 7.0 mm long and about 7.0 cm wide at base;

Stipule color: Adaxial marginal portion nearest RHS N155D with upper and longitudinal middle nearest RHS 186A, abaxial variable between RHS N155D and RHS 186A;

Peduncle: Panicle; terete; stiff; pubescent; upright; to about 45.0 cm long and 3.0 mm diameter at base, average about 42 cm tall and about 3.0 mm diameter; about twenty per plant with up to 200 flowers per panicle, average about 180; heavily-branched panicle with up to 20 branches per peduncle up to about 8.5 cm long and about 1.0 mm diameter decreasing distally, average 20 branches per panicle; branches outwardly to slightly upright; flower density moderate;

Flowering longevity: Panicle effective for about six to nine weeks;

Peduncle color: Young developing or lower portion and more shaded nearest RHS 145A, mature in high light nearest RHS 183A;

Pedicel: Terete, finely puberulent, about 2.0 mm long and 0.5 mm diameter;

Pedicel color: Between RHS 183B and RHS 183A;

Buds one day prior to opening: Ellipsoid; rounded apex and rounded base; puberulent to glandular; about 5.0 mm long and. 2.5 mm diameter;

Bud color one day prior to opening: Basal portion nearest RHS 146C, becoming nearest RHS 153C in distal one half with apex nearest RHS 153B;

Flower: Perfect, campanulate, actinomorphic, about 6.0 mm long and 4.0 mm in diameter at face; individual flowers lasting about 4 days on plant or as cut flower; persistent;

Flower attitude: Mostly outwardly;

Calyx: Five, apex acute, base fused in proximal 4.5 mm to form hypanthium; pubescent abaxial, glabrous adaxial; about 6.0 mm long and 4.0 mm wide; persistent;

Calyx color: Abaxial base between RHS 50D and RHS 50C and distally between RHS 53C and RHS 53B and RHS 53A at apex; darkening to between RHS 53A to RHS 53B with age; adaxial margin between RHS 53A and RHS 53B; proximally lightening to nearest RHS 56D at base;

Petals: Five, oblanceolate to spatulate, acute apex and fused base; margin entire, glabrous abaxial and adaxial; about 4.0 mm long and 1.5 mm wide at middle;

Petal color: Abaxial and adaxial lighter than RHS 54D or RHS 49B; adaxial and abaxial base nearest RHS 54D;

Androecium: Five adnate to adaxial calyx about 1.0 mm above base;

*Filaments*.—Five, thin, glabrous; about 2.50 mm long and less than 0.3 mm diameter; color between RHS 54D and RHS 54C.

*Anthers*.—Ellipsoidal, distinct, basifixed, longitudinal; color nearest RHS 161B.

*Pollen*.—Abundant; color nearest RHS N25A.

Gynoecium: One, two-beaked; half-inferior; bifid style with pistil split at ovary; 6.0 mm long;

*Style*.—Bifid; split apart at apex of ovary; about 4.5 mm long and about 1.0 mm diameter; color nearest RHS 53B.

*Stigma*.—Acute apex, about 0.1 mm diameter; color nearest RHS 162D.

*Ovary*.—Half-inferior, about 2.5 mm long and 2.0 mm diameter; ellipsoidal to globose, base rounded; color nearest RHS 150D.

Fruit: Two-beaked ellipsoidal capsule; about 3.0 mm long and 1.7 mm across; color nearest RHS 200B;

Seed: Thin ellipsoidal; less than 1.0 mm long and less than 0.5 mm wide; color between RHS 202A and RHS 200A;

Disease and pest tolerance: The new plant grows best with ample moisture and drainage in either sun or shade. Cold hardy from USDA zones 4 to 9. Other resistance and tolerance outside of that normal for *Heuchera* is not known.

It is claimed:

1. The new and distinct coral bells plant named *Heuchera* 'Pretty Pistachio' as herein described and illustrated.

* * * * *